United States Patent

Shuber et al.

[11] Patent Number: 5,830,665
[45] Date of Patent: Nov. 3, 1998

[54] CONTIGUOUS GENOMIC SEQUENCE SCANNING

[75] Inventors: Anthony P. Shuber, Milford; Patrick R. H. Waller, Wellesley, both of Mass.

[73] Assignee: Exact Laboratories, Inc., Maynard, Mass.

[21] Appl. No.: 808,763

[22] Filed: Mar. 3, 1997

[51] Int. Cl.[6] .............................. C12Q 1/68; C12P 19/34
[52] U.S. Cl. .............................. 435/6; 435/91.2; 935/77; 935/78
[58] Field of Search ................... 435/6, 91.2; 935/77, 935/78

[56] References Cited

U.S. PATENT DOCUMENTS

| | | | |
|---|---|---|---|
| 5,098,823 | 3/1992 | Bodmer et al. | 435/6 |
| 5,382,510 | 1/1995 | Levine et al. | 435/6 |
| 5,489,508 | 2/1996 | West et al. | 435/6 |
| 5,532,108 | 7/1996 | Vogelstein | 435/240.2 |
| 5,545,527 | 8/1996 | Stevens et al. | 435/6 |
| 5,552,283 | 9/1996 | Diamandis et al. | 435/6 |
| 5,645,986 | 7/1997 | West et al. | 435/6 |

FOREIGN PATENT DOCUMENTS

| | | |
|---|---|---|
| 0 259 031 B1 | 3/1988 | European Pat. Off. . |
| 0 390 323 A2 | 10/1990 | European Pat. Off. . |
| 0 608 004 A2 | 7/1994 | European Pat. Off. . |
| WO 95/09928 | 4/1995 | WIPO . |
| WO 95/12607 | 5/1995 | WIPO . |
| WO 96/12821 | 5/1996 | WIPO . |

OTHER PUBLICATIONS

Bodmer, Springer–Verlag, "Hereditary Colorectal Cancer", pp. 36–42 (1990).

Parker et al., Nucleic Acids Research, "Targeted gene walking polymerase chain reaction", vol. 19, No. 11, pp. 3055–3060 (1991).

Lebacq, Ann Biol. Clin., "Polymerase chain reaction and other methods to detect hot–spot and multiple gene mutations", vol. 50, pp. 709–712 (1992).

Annollés, PCR Methods and Applications, "Amplifying DNA with Arbitrary Oligonucleotide Primers", pp. 85–94 (1993).

Tisty et al., Cold Spring Harbor Symposia on Quantitative Biology, "Loss of Chromosomal Integrity in Neoplasia", pp. 645–654 (1993).

Tisty et al., Cold Spring Harbor Symposia on Quantitative Biology, "Genomic Integrity and the Genetics of Cancer", pp. 265–276 (1994).

Lisitsyn et al., Cold Spring Harbor Symposia on Quantitative Biology, "Detection of Genetic Loss in Tumors by Representational Difference Analysis", pp. 585–587 (1994).

Runnenbaum et al., Hum. Genet., "Multiplex PCR screening detects small p53 deletions and insertions in human ovarian cancer cell lines", vol. 93, pp. 620–624 (1994).

Lisitsyn et al., Proc. Natl. Acad. Sci., "Comparative genomic analysis of tumors: Detection of DNA losses and amplification", vol. 92, pp. 151–155 (1995).

Friedrich et al., Brazilian Journal of Medical and Biological Research, "Genomic characterization of type 2 polioviruses isolated from vaccine–associated cases in Brazil", vol. 28, pp. 733–742 (1995).

Schlegel et al., Cancer Research, "Comparative Genomic in Situ Hybridation of Colon Carcinomas with Replication Error", vol. 55, pp. 6002–6005 (1995).

Ried et al., Genes, Chromosomes & Cancer, "Comparative Genomic Hybridization Revals a Specific Pattern of Chromosomal Gains and Losses During the Genesis of Colorectal Tumors", vol. 15, pp. 234–245 (1996).

Primary Examiner—Carla J. Myers
Attorney, Agent, or Firm—Testa, Hurwitz & Thibeault, LLP

[57] ABSTRACT

Disclosed are methods for the detection of loss of genomic integrity characteristic of genomic instability. The methods are especially useful for detection of deletions of genomic DNA that occur in early stages of Cancer, especially colorectal cancer. Methods of the invention involve the detection in a biological sample of a nucleic acid fragment which includes both 3' and 5' DNA sequence which normally flank a region where a deletion is suspected. The assay is designed as disclosed herein such that there is only a small or negligible likelihood that the fragment will be present unless a deletion has occurred.

14 Claims, 1 Drawing Sheet

5,830,665

CONTIGUOUS GENOMIC SEQUENCE SCANNING

FIELD OF THE INVENTION

This invention relates to methods useful for deletion detection. Methods of the invention are especially useful in the detection of genomic deletions characteristic of cancer.

BACKGROUND OF THE INVENTION

Cancer is a disease characterized by genomic instability. The acquisition of genomic instability is thought to arise from a coincident disruption of genomic integrity and a loss of cell cycle control mechanisms. Generally, a disruption of genomic integrity is thought merely to increase the probability that a cell will engage in the multistep pathway leading to cancer. However, coupled with a loss of cell cycle control mechanisms, a disruption in genomic integrity may be sufficient to generate a population of genomically unstable neoplastic cells.

In one scenario, a cell undergoes a genomic disruption caused by an endogenous or exogenous carcinogen. Normally, the cell responds to such a disruption by arresting cell cycle progression. The cell may then either be repaired or discarded. However, when normal cell cycle control mechanisms are disrupted, chromosomal defects are allowed to replicate. Such defects may result in a cycle of chromosomal breaks and fusions, leading to the rearrangements and other mutations that activate oncogenes and inactivate tumor suppressors. In this way, genomic disruptions in a single cell may lead to an immortalized population of cells recognized as a tumor.

Importantly, however, tumor cells may not have the ability to preserve the mutant genome of the progenitor cell. Accordingly, as neoplasia progresses, increasing tumor cell heterogeneity is observed. Advanced neoplasias have a large and diverse array of chromosomal aberrations as compared to early neoplastic cells. The number and diversity of genomic disruptions in tumor cell populations is thought to result from the genomic instability inherent in established neoplastic cells.

Genomic instability typically results from large genomic disruptions that are observable cytologically. However, a population of genomically unstable cells may also result from relatively small disruptions in genomic integrity. Such disruptions include a loss of heterozygosity, microsatellite instability (often associated with a loss or addition of microsatellite DNA repeats, and usually indicative of defects in DNA repair mechanisms), and mutations (which include deletions, insertions, substitutions, duplications, rearrangements, or modifications). For example, the loss of heterozygosity at the p53 tumor suppressor locus has been correlated with various types of cancer. Ridanpaa, et al., *Path. Res. Pract*, 191: 399–402(1995). In addition, the loss or other mutation of the apc and mcc tumor suppressor genes has also been associated with tumor development. Blum, *Europ. J Cancer*, 31A: 1369–372 (1995).

Disruptions in genomic integrity theoretically can serve as markers for the early stages of, for example, colon cancer, and can be detected in DNA isolated from biopsied colonic epithelium and in some cases from transformed cells shed into fecal material. Sidransky, et al., *Science*, 256: 102–105 (1992). The ability to detect the first signs of a loss of genomic integrity is important in early stage cancer diagnosis. However, deletions or other mutations associated with early stages of genomic disruption appear to occur at many different sites in the genome. Furthermore, the size of a disruption at a particular locus or loci varies significantly across individual patients. Techniques, such as comparative genomic analysis, restriction fragment length polymorphism, and amplification of microsatellite sequences have been used to detect deletions in tumor cells. Lisitsyn, *Proc. Natl. Acad. Sci. USA*, 92:151–155 (1995). However, such techniques can require large amounts of DNA from the tumor cells or are not useful to detect deletions in only a subpopulation of cells in a heterogeneous biological sample. Accordingly, those techniques do not reliably detect early stages of genomic disruption, in which deletions have occurred in only a small subpopulation of cells.

Many forms of cancer are successfully treated if diagnosed early. For example, in many cases, such as colon cancer, surgical removal of cancer tissue prior to vascular invasion is highly successful. Most colon cancer diagnostics rely on the detection of extracellular indicia of cancer. However, since extracellular indicia of cancer typically occur late in the etiology of the disease, detection of events, such as loss of heterozygosity, associated with early stages of cancer would greatly increase patient survival rates. Traditional methods for the detection of molecular events that underlie early stages of cancer target well-defined sites of mutation. However, such techniques are inadequate for detecting random disruptions in genomic integrity that are typically associated with early stages of neoplasia. Moreover, because many of those techniques target specific mutations, they are especially unsatisfactory for detecting random events associated with oncogenesis.

One technique that has been proposed to avoid the limitations of targeted mutation techniques is comparative genomic hybridization. Kallioniemi, et al. *Science*, 258: 818 (1992). That technique allows detection of many duplications, amplifications and aneuploidies by comparing DNA from a population suspected to contain a mutation with normal reference DNA. However, comparative genomic hybridization requires relatively high purity of DNA, and is not convenient when cellular debris, such as that present in stool, is used as the sample.

Thus, there is a need in the art for methods of detecting loss of genomic integrity that underlie early neoplasia. Since early neoplastic events are often associated with deletion of wild-type DNA, methods of detecting deletions are an important means for diagnosing and/or screening patients for early onset of cancer. Accordingly, the invention provides methods for detecting deletions and other events indicative of neoplasia.

SUMMARY OF THE INVENTION

A new method has been discovered that allows detection of a deletion or other nucleic acid mutation by interrogating nucleic acid regions outside the region suspected to contain the mutation. In a preferred embodiment, the invention comprises detecting a nucleic acid that would not be present in sample but for a genomic disruption in the sample. The invention comprises selecting a nucleic acid, referred to herein as a diagnostic nucleic acid, at least a portion of which is suspected to be deleted. The diagnostic nucleic acid may comprise large portions of the genome. One then seeks to detect a nucleic acid, referred to herein as an indicator nucleic acid, that is the same size or smaller than the diagnostic nucleic acid, and that comprises both a region that is 3' to the diagnostic nucleic acid and a region that is 5' to the diagnostic nucleic acid. An indicator nucleic acid (comprising at least portions of regions that are 3' and 5' with respect to a diagnostic nucleic acid in a wild-type cell) will only be detected in a fragment equal to or smaller than the diagnostic nucleic acid if a deletion or other genomic disruption (e.g., a translocation) of at least part of the diagnostic nucleic acid has occurred. Accordingly, the invention generally comprises detecting the presence in a biological sample of an indicator nucleic acid indicative of a deletion or other genomic disruption of at least a portion of a diagnostic nucleic acid. As is evident below, 3' and 5' flanking regions may be chosen as a means for defining the diagnostic nucleic acid.

In a preferred embodiment, the indicator nucleic acid is detected as a fragment having hybridized thereto at least one probe complementary to at least a portion of a 3' flanking sequence, and at least one probe complementary to at least a portion of a 5' flanking sequence. As used herein, the terms "3' flanking sequence" and "5' flanking sequence" mean sequences that are 3' and 5', respectively, to a diagnostic nucleic acid. A probe may be complementary to a portion of either 3' or 5' flanking sequence that is immediately 3' or 5' to the diagnostic nucleic acid. Alternatively, a probe may be complementary to a portion of either 3' or 5' flanking sequence that is distant from the diagnostic nucleic acid. In any case, probes complementary to the 3' and 5' regions hybridize to a fragment approximately equal to or smaller than the diagnostic nucleic acid only if a deletion or other genomic disruption of at least part of the diagnostic nucleic acid has occurred. Probes complementary to distant portions of the 3' and 5' flanking sequences hybridize to the fragment only if the deletion or other genomic disruption has removed sufficient portions of the 3' and 5' flanking regions, in addition to the diagnostic nucleic acid, such that the distant 3' and 5' flanking sequences are separated by a distance approximately equal to or smaller than the length (in bases) of the diagnostic nucleic acid.

Accordingly, methods of the invention comprise detecting in a biological sample the presence of an indicator nucleic acid. An indicator nucleic acid comprises at least a portion of each of 3' and 5' flanking nucleic acids, wherein the 3' and 5' nucleic acids flank a diagnostic nucleic acid in a wild-type cell. In addition, an indicator fragment is a fragment equal to or smaller than the size of a corresponding diagnostic nucleic acid. In a preferred embodiment, probes complementary to the 3' and 5' flanking nucleic acids are detectably labeled. Also in a preferred embodiment, methods of the invention further comprise the step of producing nucleic acid fragments in the sample that are approximately the same size or smaller than the size of the diagnostic nucleic acid.

In a preferred embodiment, a sample for analysis according to the invention is selected from stool, urine, sputum, blood, lymphatic fluid, semen, biopsy tissue, cerebrospinal fluid, and pus. In a particularly preferred embodiment, the sample is a cross-section of stool. A preferred method for preparing a cross-section of stool is provided in co-owned, co-pending patent application Ser. No. 08/699,678 the disclosure of which is incorporated by reference herein. As stool passes through the colon, it adheres cells and cellular debris sloughed from colonic epithelial cells. Similarly, cells and cellular debris are sloughed by a colonic polyp (comprising mutated DNA). However, only the portion of stool making contact with the polyp will adhere sloughed cells. It is therefore preferable to obtain at least a cross-section of stool in order to ensure that the stool sample contains a mixture of all sloughed cells, including those sloughed by presumptive cancer cells (e.g., polyps).

Also in a preferred embodiment, methods of the invention comprise detecting an indicator nucleic acid comprising at least a portion of each of a 3' and a 5' flanking sequence; wherein either the 3' or 5' flanking sequence comprises at least a portion of a telomere. In a particularly-preferred method of the invention, either the 3' or 5' flanking sequence is selected from the group comprising single telomeric repeats, double telomeric repeats, and triple telomeric repeats.

Methods of the invention are preferably used to detect deletions of tumor suppressor DNA. Accordingly, in preferred methods of the invention, a diagnostic nucleic acid comprises DNA encoding a tumor suppressor protein. In a particularly preferred embodiment, the diagnostic nucleic acid comprises tumor suppressor DNA and non-tumor suppressor DNA that is immediately 3' and 5' to the tumor suppressor DNA. According to such methods, a diagnostic fragment comprising tumor suppressor DNA and flanking 3' and 5' non-tumor suppressor DNA is chosen. Oligonucleotide probes capable of hybridizing with DNA 3' and 5' of the diagnostic fragment (i.e., just outside the non-tumor suppressor 3' and 5' regions) are constructed and detectably labeled. Sample suspected to contain a deletion in tumor suppressor DNA is cut, for example, with restriction enzymes, to produce fragments, some of which are approximately equal to or smaller than the length of the diagnostic fragment (i.e., potential indicator fragments). The sample is then exposed to the labeled probes. Fragments having both 3' and 5' probes hybridized thereto, and being of a size approximately equal to or smaller than the diagnostic fragment, are indicative of a deletion in the diagnostic fragment.

In a preferred embodiment, an indicator nucleic acid is detected using complementary probes (i.e., complementary to the regions flanking the diagnostic nucleic acid). Also in a preferred embodiment, the probes are peptide nucleic acid probes (PNAs). In either case, the probes are preferably labeled. Preferred labels include radioactive labels, fluorescent labels, molecular weight labels, and enzymatic labels. Other labels are known to those of ordinary skill in the art. In a particularly preferred embodiment, 3' and 5' probes are differentially labeled (e.g., by fluorophores having distinct emission maxima). Distinct labeling is not, however, necessary in light of the ability to distinguish the intensity of one versus two labels using the labeling methods described above. Detection of an indicator nucleic acid may also be accomplished using DNA-binding proteins and other non-probe based methods. Also in a preferred embodiment, chromatographic, electrophoretic, or mass spectrometric methods are used to detect an indicator nucleic acid. Such methods may be used alone or may be used in combination with labeling methods described above.

In a particularly preferred embodiment, methods of the invention comprise detecting an indicator fragment by exposing a sample to a plurality of oligonucleotide probes, each complementary to a sequence outside a chosen diagnostic fragment (i.e., 3' and 5' flanking sequences). In particular, such methods comprise exposing the sample to a first plurality of probes, each complementary to different portions of a region 3' of the diagnostic nucleic acid, and further exposing the sample to a second plurality of probes, each complementary to different portions of a region 5' of the diagnostic nucleic acid. Sample preparation (i.e. fragmentation) may be done either before or after exposure of the sample to the probes. The probes are exposed to the sample under conditions appropriate for their hybridization to complementary nucleic acids present in the sample. Such conditions are known in the art (and may require an additional step to denature double stranded nucleic acids in the sample). Fragments equal to or smaller than the chosen diagnostic fragment, and having both a member of the first plurality and a member of the second plurality hybridized thereto, are indicative of a deletion in the diagnostic nucleic acid. In a preferred embodiment, the first and second pluralities of probes are generated by random priming of nucleic acid regions 3' and 5' with respect to the diagnostic nucleic acid.

Also in a preferred embodiment of the invention, a deletion of genomic DNA is detected by 1) selecting a diagnostic fragment suspected to contain a deletion; 2) denaturing DNA in a sample suspected to contain the diagnostic fragment; 3) exposing the sample to a plurality of reverse (antisense) primers, each complementary to a different portion of the complement of the 3' flanking DNA, and exposing the sample to a plurality of forward (sense) primers, each complementary to a different portion of a 5' flanking DNA; 4) conducting an amplification reaction using the primers; and 5) detecting an amplified fragment equal to or smaller than the size of the diagnostic fragment and having both 3' and 5' primer DNA incorporated therein. In a preferred embodiment, the 3' and 5' DNA primers are generated using random primer extension procedures on 3' and 5' flanking DNA. Also in a preferred embodiment, 3' and 5' DNA primers are detectably labeled, preferably differentially detectably labeled. Preferred amplification reactions include polymerase chain reaction and ligase chain reaction. See, e.g., U.S. Pat. No. 4,800,159, incorporated by reference herein.

Methods of the invention are useful to screen individuals for cells containing nucleic acid deletions or other genomic disruptions. For example, methods of the invention are useful in conjunction with the quantitative detection methods provided in U.S. Pat. No. 5,670,325, incorporated by reference herein. These quantitative methods comprise counting and comparing the number of hybridization events obtained in a biological sample using two differentially labeled hybridization probes, each complementary to a different genetic locus. If the number of events is statistically different for the two probes, a deletion has occurred in at least some cells in the sample at the locus complementary to the probe for which fewer hybridization events were counted. Such quantitative methods are useful both to confirm the presence of a deletion detected using the methods of the present invention, and to more precisely determine the location and size of the deletion. Finally, methods of the invention are useful to determine which patients should be scheduled for further evaluation, such as endoscopy, biopsy, or other known clinical tests.

Numerous additional aspects and embodiments of the invention are apparent upon consideration of the following detailed description thereof.

DETAILED DESCRIPTION OF THE INVENTION

Methods of the invention are useful for the detection of a deletion or other genomic disruption in nucleic acids in a biological sample. Methods of the invention are particularly useful for the detection of a deletion characteristic of genomic instability. According to methods of the invention, a deletion is detected as the presence in a sample of a nucleic acid fragment that would not be present in the sample but for a deletion. Such a nucleic acid is referred to herein as an indicator nucleic acid, and is indicative of a deletion of at least a portion of a diagnostic nucleic acid as defined herein. For purposes of the invention, a diagnostic nucleic acid is a nucleic acid, at least a portion of which is suspected of being deleted. For example, a deletion of at least a portion of a diagnostic nucleic acid, detected in a patient's stool sample, may be associated with the presence of colon cancer in the patient. Such a patient may then be exposed to invasive techniques, such as endoscopy, to detect the presence of a polyp or other abnormality. The diagnostic nucleic acid may be of any desired size. Typically, the size of the diagnostic fragment is based upon the expected size of deletion, the number of expected or suspected deletions, the availability of probes, and other considerations known to the skilled artisan. In a preferred embodiment, after the diagnostic nucleic acid is chosen, the 3' and 5' nucleic acids, which flank the diagnostic nucleic acid in a wild-type cell, are detectably labeled. The extent of the 3' and 5' nucleic acids that is labeled is also based on the expected size of deletion, the availability of probes, and other considerations known to the skilled artisan. In a most preferred embodiment, the 3' and 5' nucleic acids are labeled differently. Methods of the invention are useful to detect deletions of any combination of portions of the diagnostic nucleic acid and the flanking nucleic acids, provided at least a portion of the diagnostic nucleic acid is deleted, and provided at least a portion of each of the 3' and 5' flanking regions remain after the deletion. For purposes of the invention, the sizes of the 3' and 5' flanking regions are determined by the sizes of the nucleic acid regions (flanking the diagnostic nucleic acid) that are detectably labeled. The skilled artisan understands that either the sense or the antisense 3' and 5' regions or both the sense and the antisense 3' and 5' regions may be used to detect an indicator fragment according to methods of the invention.

Figure 1:
FIG. 1A represents a wild-type nucleic acid. No indicator nucleic acid is generated according to the methods of the invention.
FIG. 1B represents a nucleic acid wherein a portion of the diagnostic nucleic acid is deleted. The arrow points to the indicator nucleic acid.
FIG. 1C represents a nucleic acid wherein the entire diagnostic nucleic acid, and a portion of both 3' and 5' flanking nucleic acids are deleted. The arrow points to the indicator nucleic acid.
Figure 1:
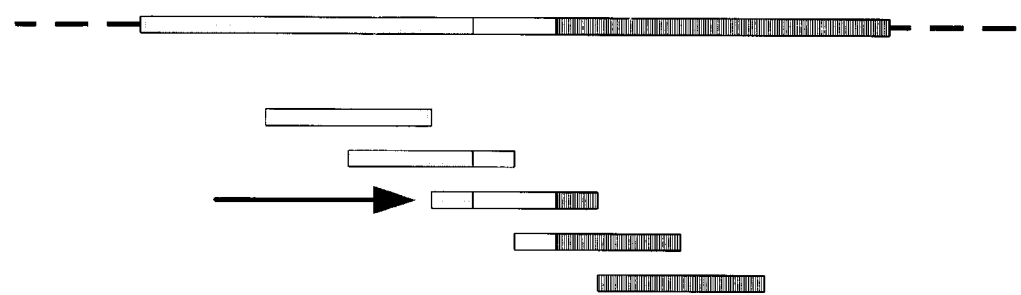
Figure 1:
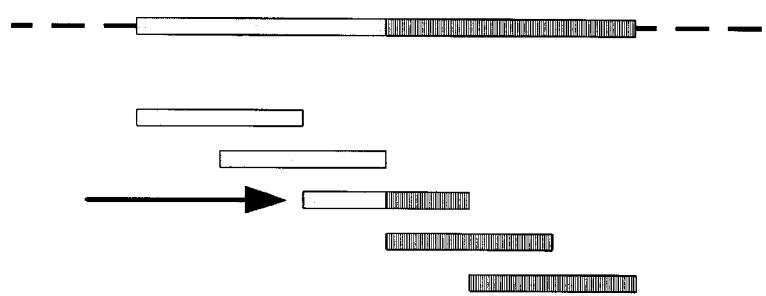

An understanding of the invention is aided by reference to FIGS. 1A–1C. FIG. 1A depicts results of an assay of the invention in which no deletion has occurred in the diagnostic nucleic acid. As shown in the top panel of FIG. 1A, a diagnostic nucleic acid (white) is flanked by a 3' nucleic acid (gray shading) and a 5' nucleic acid (stipled shading). Dashes at the ends of the nucleic acid indicate that the portion of interest to the invention may be part of a larger genomic sequence. As shown in the lower panels of FIG. 1A, when no deletion has occurred in the diagnostic nucleic and, no single fragment (i.e., fragments equal to or smaller than the diagnostic fragment) produced therefrom contains portions of both 3' and 5' flanking regions. However, as shown in FIG. 1B, a partial deletion of the diagnostic fragment results, upon fragmentation, in the presence of indicator fragments (fragments that are equal to or smaller than the diagnostic fragment and that contain portions of both 3' and 5' flanking nucleic acids, indicated by the arrow in FIG. 1B). Similarly, as shown in FIG. 1C, deletion of an entire diagnostic region and portions of both 3' and 5' flanking nucleic acids results, upon fragmentation, in the presence of indicator fragments. The portions of the 3' and 5' flanking nucleic acids that are present in the indicator fragment in FIG. 1C, are more distant from the diagnostic nucleic acid (in a wild-type cell) than the 3' and 5' portions present in the indicator fragment in FIG. 1B.

In a preferred embodiment, once the diagnostic nucleic acid is chosen, probes or other nucleotide-binding entities are constructed to bind to nucleic acids immediately 3' and immediately 5' of the diagnostic nucleic acid. In the case of oligonucleotide probes, probe length may vary. A preferred probe length is from about 5 to about 100 nucleotides, but probes of any length may be used in accordance with the invention. Especially preferred are probes generated by random priming methods discussed below. After probes are constructed, the sample is fragmented such that fragments equal to or less than the length of the diagnostic nucleic acid are produced. The sample may also contain some fragments larger than the length of the diagnostic nucleic acid (i.e., it is not necessary to make all fragments equal to or less than the diagnostic nucleic acid). The sample is then exposed to the probes. Conversely sample may be exposed to probes prior to fragmentation. The degree of hybridization stringency is selected based upon the sensitivity and specificity desired by the clinician. For example, conditions are known which promote complete hybridization (i.e. without a single base mismatch). Wallace, et. al., *Nucl. Acids Res.* 6: 3543–3557 (1979), incorporated by reference herein. A particularly preferred means for increasing specificity of probe hybridization involves the use of segmented probes as disclosed in copending U.S. patent application Ser. No. 08/815,576, incorporated by reference herein. Segmented probes are pairs of probes that are required to hybridize adjacent to each other in order for a hybridization event to be counted. A first probe is a relatively short probe (e.g., about a 4-mer to about a 16-mer) that hybridizes with high specificity, but with low stability. A second probe is longer and tolerates hybridization mismatches, but binds with high stability. The first and second probes are required to hybridize to substantially contiguous genomic regions (separated by between about 5 and zero nucleotides). Adjacent hybridization stabilizes the short probe and lends overall specificity by requiring adjacent hybridization at the melting temperature of the short probe.

Regardless of the method used, a deletion is detected as a fragment equal to or smaller than the diagnostic fragment that has both a 3' and 5' probe bound thereto. Such will be the case in a fragment of the required size when a deletion or other genomic disruption of the region intervening between the probe sequences occurs. The deletion can be the entire diagnostic nucleic acid, or any portion thereof, and can include a portion of one or both 3' and 5' flanking nucleic acids as long as the fragment size inspected for the presence of both 3' and 5' probes is approximately equal to or smaller than the diagnostic fragment.

Methods of the invention provide many advantages over deletion detection methods of the art. Traditional methods for deletion detection involve restriction fragment length polymorphisms or comparative genome hybridization analysis, and rely upon the use of relatively homogeneous populations of cells containing the deletion. Alternatively, methods in the art require prior knowledge of the expected deletion size. In contrast, methods of the invention do not require sophisticated quantitative analysis or labor-intensive cloning and sequencing procedures to detect the presence of a deletion in a biological sample. As described above, methods of the invention are useful to detect deletions of unknown size, provided at least a portion of the diagnostic region is deleted. Additionally, methods of the invention are used to detect the presence of a deletion whether it is present in only a small subpopulation of cells in a sample or in the majority or all of the cells in a sample.

Accordingly, methods of the invention detect the presence of a deletion in a biological sample by detecting the presence of nucleic acids, wherein the distance separating two genomic regions is smaller than the distance separating those two regions on a wild-type chromosome. Nucleic acid fragments useful to detect the presence of a deletion of at least a portion of a diagnostic nucleic acid that is flanked at opposite ends by 3' and 5' nucleic acids are approximately equal to or smaller than the size of the diagnostic nucleic acid. Use of fragments approximately equal to or smaller than the diagnostic nucleic acid prevents false positive detection, because a fragment of that size contains portions of both the 3' and 5' nucleic acids only if a deletion of at least a portion of the diagnostic nucleic acid has occurred. Use of DNA fragments that are smaller than the size of the diagnostic nucleic acid will lead to false negative results if the deletion removes only a portion of the diagnostic nucleic acid and the DNA fragments being interrogated for the presence of portions of both 3' and 5' nucleic acids are smaller than the mutant diagnostic nucleic acid resulting from the deletion.

In a preferred embodiment, methods of the invention broadly comprise obtaining a biological sample containing DNA, identifying a diagnostic nucleic acid at least a portion of which is suspected of being deleted, detectably labeling 3' and 5' nucleic acids which flank opposite ends of the diagnostic nucleic acid in a wild-type cell, fragmenting the DNA (the DNA may be fragmented prior to or subsequent to the labeling step) and detecting DNA fragments containing label from both 3' and 5' nucleic acids. A DNA fragment that is shorter than the diagnostic nucleic acid and that contains portions of both 3' and 5' nucleic acids is indicative of the presence of DNA having a deletion or other genomic disruption of at least a portion of the diagnostic nucleic acid. Similarly, a DNA fragment that is approximately the same size as the diagnostic nucleic acid, and that contains label from both 3' and 5' nucleic acids, is indicative of the presence of a deletion or other genomic disruption of at least a portion of the diagnostic nucleic acid. For the purposes of the present invention, a DNA fragment is regarded as approximately the same size as the diagnostic nucleic acid if any size difference does not generate false positive results due to the fragment being sufficiently long to contain label from both 3' and 5' nucleic acids when the fragment is derived from wild-type genomic DNA in which no deletion has occurred.

The invention may be divided into three general embodiments. (1) subtelomeric deletion detection; (2) interstitial deletion detection; and (3) patient-specific therapy using information from the detection methods of the invention. Each of these general embodiments is discussed below.

I. SUBTELOMERIC DELETIONS

A subtelomeric deletion is defined herein as a deletion of genomic region that is contiguous with a telomeric region. Studies of chromosomes derived from cancerous tissue have shown that cancer cells often contain deletions of chromosome arms extending to and including subtelomeric DNA. The detection of subtelomeric deletions is therefore a potentially useful indicator of the presence of cancerous cellular material in a biological sample. Using methods of the invention, the presence of a subtelomeric deletion is detectable as the presence of telomeric nucleic acid (one or more telomeric repeat) that is contiguous with a region that is normally separated from the telomeric nucleic acid by subtelomeric DNA in the wild-type genome. Vertebrate telomeres comprise repeats of the sequence TTAGGG. Thus, all or a portion of the subtelomeric DNA is the diagnostic nucleic acid. The telomeric DNA and the DNA bordering the subtelomeric DNA on the side closest to the centromere represent the 3' and 5' nucleic acids discussed above. The indicator fragments are approximately equal to or less than the size of the subtelomeric region or portion thereof selected for investigation.

In one embodiment, a subtelomeric deletion is detected as a genomic DNA fragment to which are bound both telomere-specific probes and probes derived from a library that contains neither telomeric nor subtelomeric DNA. Probes made from the library preferably do not hybridize to either telomeric or subtelomeric sequences. The size of the subtelomeric regions excluded from the probe library depend on the library that is used. In a preferred embodiment, the probe library is derived from a single chromosome arm, excluding both the subtelomeric region and the telomeric DNA of that arm. Probe libraries are used to detect subtelomeric deletions according to the invention. In such methods, a fragment approximately equal to or smaller than the subtelomeric region is indicative of a deletion if it hybridizes with both a member of the non-telomeric probe library and with a telomeric probe. Probe libraries comprising non-subtelomeric sequences are derived by random primer extension of DNA on the chromosome of interest (e.g., chromosome 17). The subtelomeric region is excluded either prior to random priming or the complement to subtelomeric DNA is removed after random priming (by, e.g., subtractive hybridization as reported in Tartof, *Recombinant DNA Methodology II*, Wu (ed.), 233–319 (1995), incorporated by reference herein).

In another embodiment, methods of the invention comprise obtaining DNA fragments representative of the genomic DNA in a biological sample. The fragments are then contacted with two sets of specific probes under hybridization conditions sufficiently stringent to promote specific hybridization. See, e.g., *Short Protocols in Molecular Biology*, Ausubel, et al. (eds.) (3d Ed., 1995), incorporated by reference herein. The fragments may be exposed to the probes either simultaneously or sequentially. The first set of probes is specific for telomeric sequences. The length of the probe is sufficient to specifically hybridize to the telomeric region under the appropriate hybridization conditions. The second set of probes comprises a library of probes complementary to genomic sequences of a given chromosome arm, excluding the telomeric and the subtelomeric regions.

In a preferred embodiment, the size of the majority of DNA fragments obtained from the biological sample is similar to, or smaller than, the size of the subtelomeric region. For example, the subtelomeric region may be defined as the genomic region between the region defined by the first set of probes and the region defined by the second set of probes. The first and second sets of probes are preferably differentially labeled. The method further comprises performing an assay to detect an indicator fragment hybridized to probes from both the first and second sets of probes. Such a DNA fragment contains nucleic acid sequences from the regions normally flanking the subtelomeric region in a wild-type cell, and is therefore indicative of a deletion in the subtelomeric region. The deletion may comprise only part of the subtelomeric region, or it may comprise the entire subtelomeric region and include part of one or both of the flanking regions. A deletion that encompasses most of the chromosome arm will be detected according to this method, provided that part of each of the two regions, defined respectively by the first and second set of probes, remains on the chromosome.

Methods described above may also be used to detect genomic disruptions other than deletions. For example, methods of the invention may be used as described above to detect translocations, unequal crossovers, and other disruptions that cause a portion of wild-type DNA to be deleted or misplaced.

II. INTERSTITIAL DELETIONS

Methods of the invention are also useful for detecting interstitial deletions, defined herein as deletions which do not comprise subtelomeric DNA. Methods for detecting interstitial deletions are similar to methods for detecting subtelomeric deletions. Interstitial deletions in any region of the genome may be detected according to methods of the invention. Accordingly, a diagnostic region is first selected. Then, a deletion is detected with one or more probes complementary to a 3' region flanking the diagnostic region and one or more probes complementary to a 5' region flanking the diagnostic region. A deletion in the diagnostic region is detected as an indicator fragment to which both a 3' and a 5' flanking probe hybridize.

In a preferred embodiment, two sets of hybridization probes are used. A first set of probes comprises a library of probes complementary to a 3' region that flanks a chosen diagnostic nucleic acid in a wild type cell. A second set of probes comprises a library of probes complementary to a 5' region flanking the diagnostic nucleic acid. In a preferred embodiment, both libraries are derived from the same side of the centromere of a given chromosome. A biological sample being assayed for the presence of deletions is tested with a series of library sets specific for each chromosome half. These tests can be performed in parallel assays or in a single pooled assay. In the case of a single pooled assay, the presence of a positive signal is indicative of at least one deletion somewhere in the genome. In the case of the assays carried out in parallel, the presence of a positive signal specifically indicates which chromosome half, or which set of chromosome halves, contain(s) the deletion. Interstitial regions of interest for practicing the invention include genes encoding tumor suppressor proteins such as p53, apc, dcc and mcc, and oncogenes, such ras. Detection of deletions in microsatelite regions is also a preferred use of methods of the invention.

III. DNA FRAGMENTATION METHODS

In preferred methods of the invention, the genomic DNA is fragmented to yield fragments of a size approximately equal to, or smaller than, the size of a diagnostic nucleic acid. The fragmentation method preferably produces fragments that are uniform in size. However, some fragments larger than the diagnostic nucleic acid may be produced. In addition, the sites of fragmentation preferably are random, thus generating a set of appropriately sized random fragments comprising an indicator fragment regardless of the location of the deletion endpoints (which may be random). The DNA in a biological sample is fragmented by sonication or mechanical shearing methods known in the art. Sonication or shearing techniques yield fragments that are uniform in size, and the size is determined by the degree of sonication or shearing to which the sample is exposed. Sonication and shearing techniques also generate random DNA fragments. Alternatively, the sample is treated with one or more DNA endonucleases or exonucleases. For example, a partial DNase treatment yields random fragments that are approximately uniform in size. The relative amount of DNase used and the duration of the treatment will determine the average size of the resulting fragments. Alternatively, the sample is treated with one or more specific restriction endonucleases.

Fragments representative of the genomic DNA in the biological sample are also generated by limited total genomic amplification using random primers. The size of the amplified fragments is determined by the relative concentrations of the random primers and the template, and the length of the extension reaction in the amplification procedure. In a preferred embodiment, to detect subtelomeric deletions, the genomic DNA in the biological sample is amplified using a mixture of random primers and telomere-specific primers. This procedure enriches the sample in DNA fragments containing telomeric DNA. If a subtelomeric deletion is present, DNA fragments indicative of the deletion are expected to be among the fragments containing telomeric DNA.

IV. DNA LABELING AND PROBE CONSTRUCTION

In a preferred embodiment first and second genomic regions bordering a diagnostic nucleic acid are labeled using hybridization probes. Such probes may comprise DNA, RNA or PNA, and are detectably labeled using methods known in the art. In one embodiment probes are labeled with radioactive isotopes such as $^{32}P$, $^{33}P$, $^{35}S$, $^{125}I$, or any other detectable isotope useful for labeling a hybridization probe. In an another embodiment, probes are labeled with fluorescent molecules. Numerous fluorescent labels are known in the art, and any detectable fluorescent probe label is useful for practice of the invention. Alternatively, probes are attached to moieties which increase their molecular weight. For example a probe may be directly attached to a glycoprotein, or a glass bead, or any compound which has a detectable effect on the molecular weight of the probe. In a further embodiment, probes are labeled with a compound that is detectable due to specific interactions with an additional compound. For example, biotinylated probes are detectable via interaction with streptavidin. The streptavidin moiety is attached to a detectable label such as a bead, a fluorescent tag, or an enzyme. In another example, the probes are labeled with a hapten or other antigen which is specifically recognized by an antibody. The antibody is made detectable using methods known in the art including radioactive isotopes, fluorescent tags, and enzyme reactions. In a further example the probes are directly attached to an enzyme which is detectable via a specific enzyme catalyzed reaction generating a detectable product.

In a preferred embodiment, hybridization probes that are specific for the first and second genomic regions are identified using detectably different labels. For example, a probe that hybridizes specifically with a first genomic region is labeled with a fluorescent tag, and a probe that hybridizes specifically with a second genomic region is labeled with a molecular weight marker such as a bead. A DNA fragment that hybridizes to both probes will be detected as a fluorescent DNA fragment having increased molecular weight.

First (3') and second (5') genomic regions may be labeled with multiple probes. To prevent false positive results, it is important that the probes do not hybridize to nucleic acids present in both 3' and 5' genomic regions. This is achieved, in part, by using region-specific probes under high stringency hybridization conditions. However, even under such conditions, false-positive results may result due to the presence of repeated nucleic acid sequences throughout the genome. There exist families of known DNA repeats common to the human genome. For example, Alu repeats are present in multiple copies in the genome. Also, a DNA fraction known as cot1 DNA contains most of the highly repetitive DNA sequence elements present in the genome. The addition of cot1 DNA in vast excess during the hybridization of labeled probe to genomic DNA reduces the number of cot1 specific probes hybridizing to the genomic DNA being interrogated. This reduces the number of false positive results due to differentially labeled probes hybridizing to cot1 sequences in either the 3' or 5' genomic regions. In addition to DNA sequence elements that are repeated throughout the genome, DNA contains short sequences that are repeated throughout the genome. For example, any given tetramer is present an average of every 256 bases ($4^4$ bases) in a random genome. Accordingly, in a preferred embodiment, hybridization probes are of sufficient length to represent a sequence that occurs only once in a random genome. For example, a 16-mer is present, on average, once every 4,294,967,296 bases ($4^{16}$ bases). Therefore, any 16-mer is present an average of one time in the human genome (approximately $3 \times 10^9$ bases). Hybridization probes shorter than 16 bases may, however, be used. The size of 3' and 5' regions probed may be reduced in order to allow the use of shorter probe sequences, while not significantly increasing false positive signals. For example, an 8-mer that is exactly complementary to a 3' flanking sequence is expected to occur only once in a sequence about 65,000 base pairs. Accordingly, the use of 3' and 5' flanking regions shorter than about 65,000 bases should enable one to generate a plurality of probes, most of which are unique to either the 3' or the 5' region. Generally, the probability of any probe being present in both the 3' and the 5' region decreases with increasing probe length and/or decreasing length of 3' and 5' regions.

Hybridization probes useful for methods of the invention are synthesized by chemical synthesis methods or by template-directed enzymatic reactions. Chemical synthesis methods are used to produce DNA and PNA oligomers of a desired length and sequence. DNA and RNA probes useful for methods of the invention are also synthesized by template-directed enzymatic reactions known in the art. The average length of probes synthesized using these reactions can be varied by varying the reaction conditions, as discussed in the art. Detectable labels can also be introduced during template-directed probe synthesis. A particularly preferred probe is a peptide nucleic acid or PNA. Peptide nucleic acids are well-known. See Pluskal, et al., The FASEB Journal, Poster #35 (1994). They are synthetic oligoamides comprising repeating amino acid units to which adenine, cytosine, guanine, thymine or uracil are attached. See Egholm, et al., *Nature*, 365: 566–568 (1993); Oerum, et al. *Nucl. Acids Res.*, 23: 5332–36 (1993); *Practical PNA: Identifying Point Mutations by PNA Directed PCR Clamping*, PerSeptive Biosystems Vol. 1, Issue 1 (1995). Peptide nucleic acid synthons and oligomers are commercially available form PerSeptive Biosystems, Inc., Framingham, Mass. See, e.g., PCT publications EP 92/01219, EP 92/01220, US92/10921. In many applications, PNA probes are preferred to nucleic acid probes because, unlike nucleic acid/nucleic acid duplexes, which are destabilized under conditions of low salt, PNA/nucleic acid duplexes are formed and remain stable under conditions of very low salt. Additionally, because PNA/DNA complexes have a higher thermal melting point than the analogous nucleic acid/nucleic acid complexes, use of PNA probes can improve the reproducibility of blotting assays.

Finally, in an alternative embodiments of the invention, the 3' and/or 5' genomic regions are labeled using methods that do not involve hybridization. For example, methods of the invention may be practiced with DNA binding proteins that specifically bind to nucleic acids of the 3' or 5' genomic regions. These DNA binding proteins are detectably labeled using any appropriate method. Alternatively, antibodies are raised against specific nucleic acids. For example, antibodies which specifically bind to telomeric DNA are useful for detecting subtelomeric deletions using methods of the invention. Other DNA labeling techniques may also be used to practice the invention. Preferred techniques detectably label specific regions of the genome.

V. DETECTION METHODS

In a general embodiment, methods of the invention comprise detecting a deletion of at least a portion of a diagnostic nucleic acid by detecting an indicator nucleic acid that 1) is approximately equal to or smaller than the size of the diagnostic nucleic acid, and 2) comprises a portion of each of 3' and 5' nucleic acids which flank the diagnostic nucleic acid in a wild-type cell. In a preferred embodiment, the indicator fragment is detected as having hybridized thereto a member of a first set of hybridization probes complementary to the 3' flanking nucleic acid, and a member of a second set of hybridization probes complementary to the 5' flanking nucleic acid, wherein the first and second sets of hybridization probes are distinctly labeled. The following techniques are exemplary of those that can be used.

In a preferred embodiment, members of the first set of hybridization probes, complementary to the 3' flanking nucleic acid, are labeled with a high molecular weight tag, for example streptavidin. Members of the second set of hybridization probes are labeled with a fluorescent tag, for example fluorescein. The first and second set of probes are hybridized to fragmented DNA from a biological sample, wherein the DNA fragments are approximately equal to or smaller than the size of the diagnostic nucleic acid. The hybridization products are separated using gel electrophoresis, and the migration of fluorescently labeled products is observed. An indicator nucleic acid is detected as a fluorescent hybridization product migrating above a threshold size characteristic of a DNA fragment that 1) is approximately equal to the size of the diagnostic nucleic acid, and 2) is entirely covered by fluorescently labeled probes. In a preferred embodiment, the molecular weight tag is large enough to impart a size larger than the threshold size to a DNA fragment that 1) is approximately equal to or smaller than the size of the diagnostic nucleic acid and 2) has bound thereto one member of the first set of hybridization probes and one member of the second set of hybridization probes. This embodiment provides a high degree of sensitivity, because a fluorescently labeled probes bound to wild-type DNA fragments migrates faster in the gel than a fluorescently labeled probe bound, along with a probe having a molecular weight tag, to an indicator nucleic acid. The fluorescence due to probes bound to non-indicator nucleic acids will therefore not interfere with fluorescence due to probes bound to an indicator nucleic acid.

In an alternative embodiment, members of the first set of hybridization probes (complementary to portions of a 3' nucleic acid flanking the diagnostic nucleic acid in a wild-type cell) are attached to a solid support, for example a multiwell plate, using methods known in the art. Members of the second set of hybridization probes (complementary to portions of a 5' nucleic acid flanking the diagnostic nucleic acid in a wild-type cell) are labeled with a detectable marker, such as a fluorescent tag. DNA fragments approximately equal to or smaller than the diagnostic nucleic acid are exposed to the first and second sets of probes under hybridization conditions in, for example, a well of the multiwell plate. After hybridization, the well is washed to remove non-hybridized DNA and probes. An indicator nucleic acid is detected as the presence of a fluorescently labeled probe that remains bound in the well. The fluorescently labeled probe is bound via hybridization to the indicator fragment, which is hybridized to a member of the first set of probes attached to the well.

In an alternative embodiment, the first hybridization probe is labeled with a first moiety that binds specifically and reversibly to a first binding entity under appropriate conditions. The second hybridization probe is labeled with a second moiety that binds specifically and reversibly to a second binding entity under appropriate conditions. DNA fragments approximately equal to or smaller than the diagnostic nucleic acid are exposed to the first and second sets of probes under hybridization conditions. The hybridization products are then passed through a column having attached thereto the first binding entity under conditions to promote specific binding of the first moiety to the first binding entity. This column binds the first hybridization probes, including probes hybridized to DNA fragments. The column is then washed to remove unbound DNA and probes. The bound probes and DNA are then specifically eluted, and the eluate is passed through a second column having bound thereto the second binding entity under conditions to promote specific binding of the second moiety to the second binding entity. This second column binds second hybridization probes that are hybridized to DNA fragments present in the eluate from the first column, because no unbound second hybridization probes is present in the eluate. After washing the second column, the only DNA remaining bound is DNA having bound thereto a second hybridization probe (and a first hybridization probe, because it was present in the eluate from the first column). This DNA is then eluted from the second column and its size is observed. The size is observed using techniques known in the art, such as gel electrophoresis, chromatography, or mass spectroscopy. These techniques may require denaturing the DNA and hybridization probes.

As an alternative, detection is accomplished in a single column. Sample DNA is fragmented into pieces about the size of a diagnostic fragment or smaller. One or more labeled probes against the 3' flanking region are exposed to the sample for hybridization. After hybridization, sample is passed over a column on which 5' flanking probe has been immobilized. The column is washed to remove unbound sample and 3' probes. The attached 5' flanking probes are then released from the column. Any fragments equal to or less than the size of the diagnostic region and having both 3' and 5' probes attached thereto means a deletion or other genomic disruption has occurred (i.e., the fragment is an indicator fragment). As a further alternative, sample may be passed over the column prior to binding the 3' probe. The skilled artisan appreciates that either 3' or 5' probe may be bound in a column.

Other methods of detecting fragments that are 1) approximately equal to or smaller than the diagnostic nucleic acid, and 2) contain nucleic acid sequences from both 3' and 5' genomic regions are also useful to practice methods of the invention and are known in the art.

VI. CANCER THERAPEUTIC/METHODS

Methods of the invention are also useful as an alternative means of oligonucleotide-based cancer therapy. Upon deletion of at least a portion of a diagnostic nucleic acid, genomic regions are joined together resulting in the formation of a newly-contiguous indicator nucleic acid. Once detected, an indicator DNA fragment containing the newly contiguous nucleic acid is analyzed, using methods known in the art, to determine the nucleotide sequence at the deletion junction. Subsequently, first and second hybridization probes are synthesized, corresponding respectively to the 3' and 5' ends of the genomic nucleic acids at the deletion junction. The first and second hybridization probes are attached to first and second complementary cytolyte subunits, respectively. Each subunit is non-functional unless it is in close proximity to another subunit. When exposed to a wild-type genome, the first and second hybridization probes bind to genomic nucleic acids which are separated by the region that is deleted in the mutant genome. In this configuration, the first and second cytolyte subunits are not close enough to form an active cytolyte. When exposed to a genome containing the deletion identified above, the first and second hybridization probes bind next to each other, on either side of the deletion junction. In this configuration, the first and second cytolyte subunits are close enough to be active and kill the cell harboring the deleted genome.

The therapeutic methods of the invention have a number of advantages over current therapies based on antisense oligonucleotides, and overcome some of the significant obstacles that have plagued this field:

1) Therapeutic methods of the invention require only a single coincidence hybridization event to kill the cell containing a deletion. Antisense oligonucleotide therapies known in the art target the RNA of over-expressed oncogenes in an attempt to reduce or prevent translation of the RNA. This means that it is necessary to introduce significant amounts of antisense oligonucleotides into cells overexpressing the oncogenes. A problem with antisense technology is that the large amount of oligonucleotide necessary to shut down translation is often greater than the level of intracellular annealing stringency. Therapeutic methods of the invention overcome this hybridization problem by requiring much less hybridization probe than currently available oligonucleotide based approaches.

2) Due to the limited amount of oligonucleotide taken up by target cells, traditional antisense therapy generally involves treatment with large amounts of antisense oligonucleotides which often leads to undesirable side effects. Therapeutic methods of the invention only necessitate the introduction less hybridization probes into any one cell. Therefore, the amount of therapeutic probe needed is significantly reduced, which reduces or eliminates the undesirable side effects currently observed in antisense therapy.

3) Antisense oligonucleotide based therapies target RNA in the cytoplasm. Therapeutic methods of the invention are useful to target genomic DNA. Therefore, cells undergoing mitosis (when the nuclear membrane is not present) are good targets for therapy according to the invention.

4) In contrast to antisense therapy, therapeutic methods of the invention require two hybridization events to induce cell death, not one. Therefore, coupled with the small amount of hybridization probe that is required within the cell, the likelihood of non-specific cell killing is very low.

In a preferred embodiment, the complementary cytolyte subunits do not form a functional cytolyte if they encounter each other free in solution. In one embodiment, the subunits require the conformational constraints imposed upon them by being attached to a bound hybridization probe. In an alternative embodiment, the subunits have a very low affinity for each other, but form a functional cytolyte when they are brought together by hybridization probes bound next to each other on either side of a deletion junction.

The methods of the invention therefore provide a therapy that is patient specific. The first and second hybridization probes are designed using knowledge about the deletion obtained using the detection methods of the invention. The therapy is also highly cell specific, only killing cells that contain the specific deletion.

VII. SUPPRESSOR GENE MAPPING

Within genomics research there is continuing effort to identify disease-associated genes. Using methods of the invention, deletion databases are established for various cancers. As described above, methods of the invention are useful for detecting deletions anywhere along a chromosome and for identifying gross interstitial deletions. The invention is therefore useful to perform LOH analysis on whole chromosomes or on the whole genome. In addition, the LOH associated nucleic acid fragments can be purified away from normal fragments and sequenced, as described above. Probes can then be made for in situ hybridization and library screening. As LOH databases are developed, as with colon cancer, specific areas ("hot spots") of frequent LOH will be identified. This allows identification of specific cancer associated suppressor genes that are located in high frequency regions of LOH. In this manner, methods of the invention expedite the mapping and subsequent cloning of new suppressor genes. A significant rate limiting step in the identification and cloning of suppressor genes results from difficulties associated with analyzing large numbers of samples of heterogeneous cell populations quickly and effectively. The present invention provides methods that are useful for efficient analysis of biological samples to identify any deletions, even if they are present in only a subpopulation of cells in the sample. Additional aspects and advantages of the invention are apparent upon consideration of the foregoing diagnostic theory.

We claim:

1. A method for detecting the presence of a genomic disruption in a nucleic acid sample, comprising the steps of:
   (a) identifying a diagnostic nucleic acid region in which a genomic disruption is suspected;
   (b) identifying at least a portion of a 3' nucleic acid and at least a portion of a 5' nucleic acid, each of which flanks a wild-type diagnostic nucleic acid region that does not contain a genomic disruption;
   (c) obtaining a nucleic acid fragment from the nucleic acid sample having a length equal to or less than the length of said wild-type diagnostic nucleic acid; and
   (d) determining whether said fragment contains any of said 3' nucleic acid or said 5' nucleic acid,
   the presence of at least a portion of both said 3' nucleic acid and said 5' nucleic acid being indicative of a genomic disruption in said diagnostic nucleic acid region.

2. The method of claim 1, wherein said genomic disruption is a deletion.

3. The method of claim 1, wherein said portion of a 3' nucleic acid and said portion of a 5' nucleic acid each are detectably labeled.

4. The method of claims 1, 2, or 3, wherein said method is conducted on a stool sample or on a homogenate of a stool sample.

5. The method of claims 1, 2, or 3, wherein said method is conducted on a sample selected from the group consisting of urine, sputum, blood, lymphatic fluid, semen, and tissue biopsy.

6. The method of claims 1 or 3, wherein said genomic disruption is present only in a subpopulation of nucleic acids contained in a biological sample.

7. The method of claim 1, wherein one of said 3' or 5' nucleic acids comprises at least a portion of a telomere.

8. The method of claim 1, wherein said diagnostic nucleic acid region comprises DNA encoding a tumor suppressor protein.

9. The method of claim 3, wherein said 3' nucleic acid and said 5' nucleic acid each comprise a different detectable label.

10. The method of claim 3 or 9, wherein said detectable label is selected from the group consisting of fluorescent labels, radioactive labels, and molecular weight labels.

11. The method of claim 1, wherein said determining step is conducting using a technique selected from the group consisting of electrophoresis, chromatography, enzyme-linked immunosorbent assay, and spectrometry.

12. A method for detecting the presence of a genomic disruption in a nucleic acid sample, comprising the steps of:

(a) identifying a diagnostic nucleic acid region in which a genomic disruption is suspected;

(b) exposing a sample to a first plurality of primers, each of which is complementary to a different portion of a first genomic region in the sample;

(c) exposing said sample to a second plurality of primers, each of which is complementary to a different portion of a second genomic region in the sample, wherein said first and second genomic regions flank opposite ends of a wild-type diagnostic nucleic acid region that does not contain a genomic disruption;

(d) conducting a nucleic acid amplification reaction;

(e) identifying an amplified nucleic acid fragment having a length equal to or less than the length of a wild-type diagnostic region that does not contain a genomic disruption; and (f) determining whether said amplified nucleic acid fragment comprises a first sequence that is identical to a portion of said first genomic region and a second sequence that is identical to a portion of said second genomic region, the presence of each of said first and second sequences being indicative of a genomic disruption in said diagnostic nucleic acid region.

13. The method of claim 12, wherein at least one of said first and second pluralities of primers is generated in a random-primer extension reaction.

14. A method for screening biological samples to identify a nucleic acid deletion, the method comprising the steps of:

(a) labeling a 3' and a 5' nucleic acid in a biological sample, wherein said 3' and 5' nucleic acids flank a wild-type diagnostic nucleic acid that does not contain a genomic disruption;

(b) fragmenting nucleic acids in said biological sample; and (c) detecting a fragment that 1) is of a size equal to or smaller than that of said diagnostic nucleic acid, and 2) comprises at least a portion of each of said 3' and 5' nucleic acids, the presence of such a fragment being indicative of a deletion of at least a portion of the diagnostic nucleic acid in the biological sample.

* * * * *